(12) United States Patent
Anderson, Jr.

(10) Patent No.: US 11,457,988 B1
(45) Date of Patent: Oct. 4, 2022

(54) GLOVE DISPENSING SYSTEM AND GLOVES FOR USE THEREIN

(71) Applicant: John H. Anderson, Jr., Nederland, TX (US)

(72) Inventor: John H. Anderson, Jr., Nederland, TX (US)

(*) Notice: Subject to any disclaimer, the term of this patent is extended or adjusted under 35 U.S.C. 154(b) by 0 days.

(21) Appl. No.: 17/333,369

(22) Filed: May 28, 2021

Related U.S. Application Data

(60) Provisional application No. 63/069,834, filed on Aug. 25, 2020, provisional application No. 63/034,693, filed on Jun. 4, 2020.

(51) Int. Cl.
  *A61B 42/40* (2016.01)
  *A41D 19/00* (2006.01)
  *A61B 50/20* (2016.01)

(52) U.S. Cl.
  CPC .............. *A61B 42/40* (2016.02); *A41D 19/00* (2013.01); *A61B 50/20* (2016.02)

(58) Field of Classification Search
  CPC ..................................................... A61B 42/40
  See application file for complete search history.

(56) References Cited

U.S. PATENT DOCUMENTS

| | | | |
|---|---|---|---|
| 8,960,493 B1* | 2/2015 | Dennison | A61B 42/50 221/33 |
| 2010/0012674 A1* | 1/2010 | Brownlee | A47K 10/3612 221/199 |
| 2014/0263394 A1* | 9/2014 | Horian | A47G 21/12 221/192 |

* cited by examiner

*Primary Examiner* — Gene O Crawford
*Assistant Examiner* — Ayodeji T Ojofeitimi
(74) *Attorney, Agent, or Firm* — Bushman Werner, P.C.

(57) ABSTRACT

A glove dispensing system wherein there are a pair of tines which are adapted to be attached to, laterally spaced, and project laterally outwardly from a support. A plurality of gloves, each of which has a peripherally extending cuff forming a back wall and a front wall, the back wall having laterally spaced perforations which allow the gloves to be fitted over the tines, the back wall and front wall cooperating to form a mouth into the gloves such that a user's hand can be inserted into the gloves with a minimal amount of manual manipulation.

20 Claims, 4 Drawing Sheets

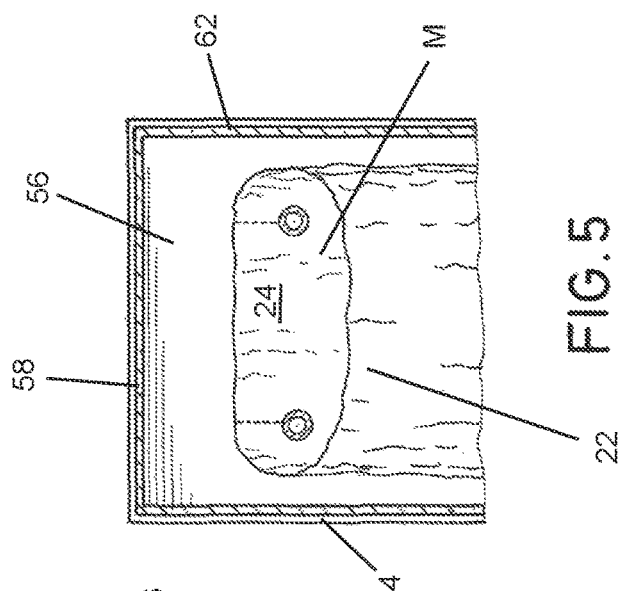
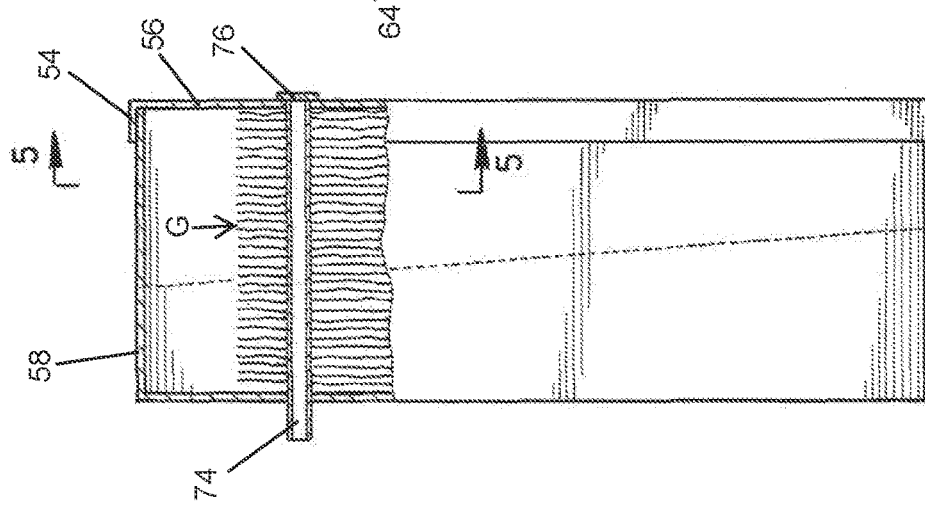
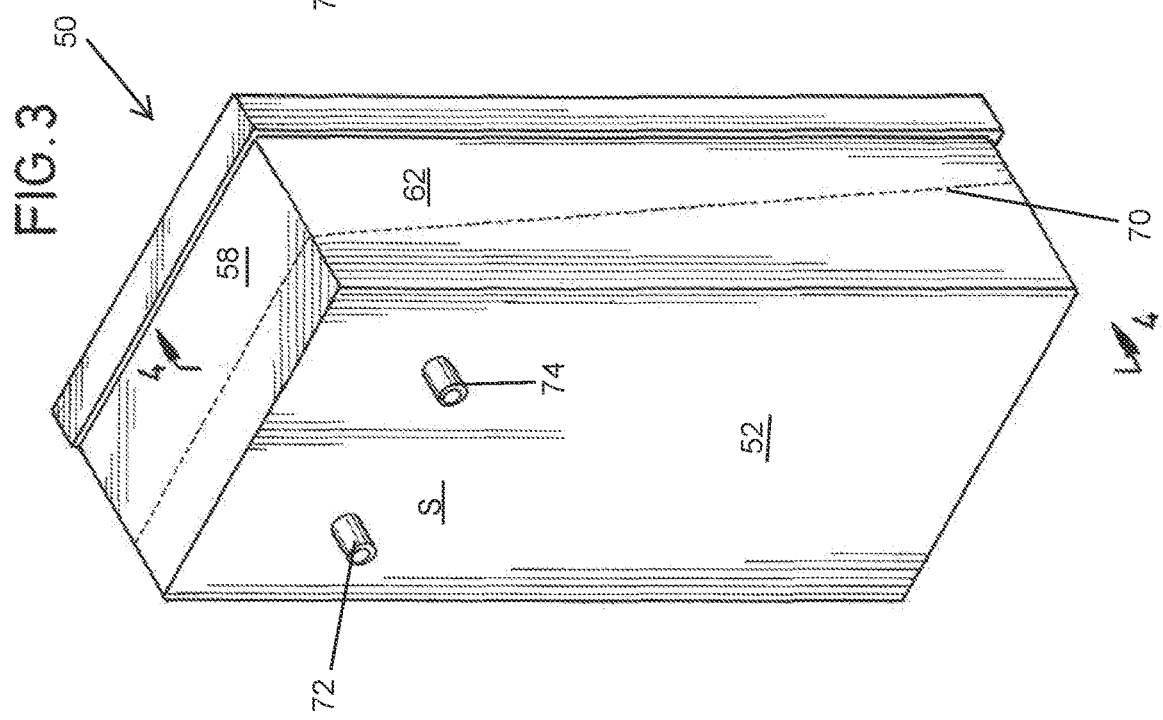

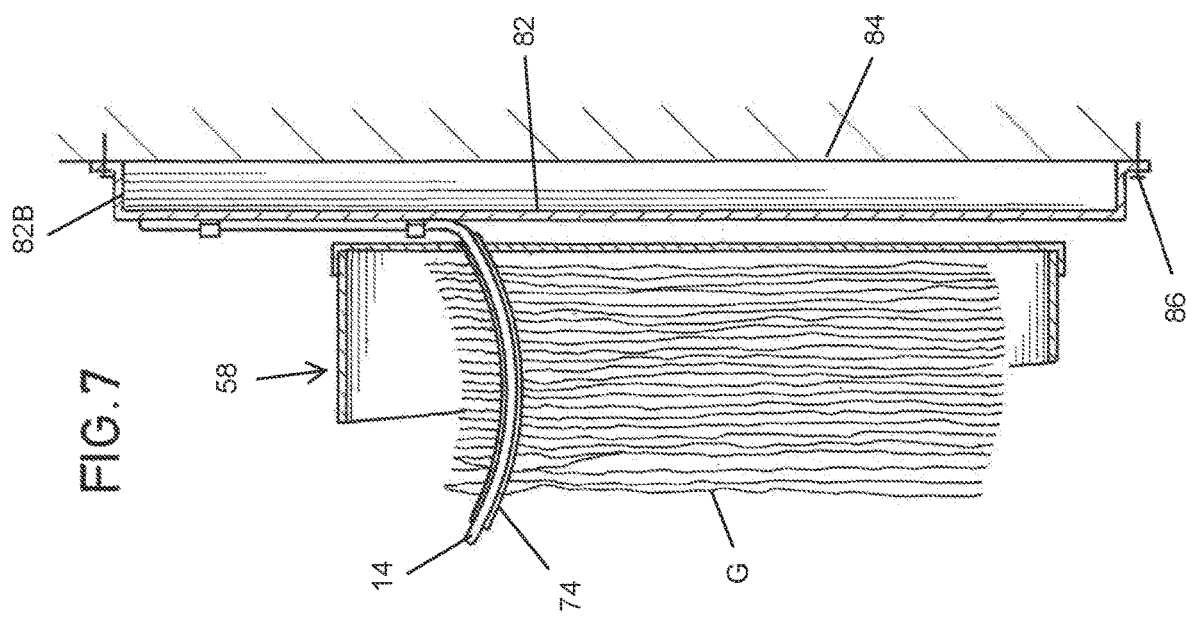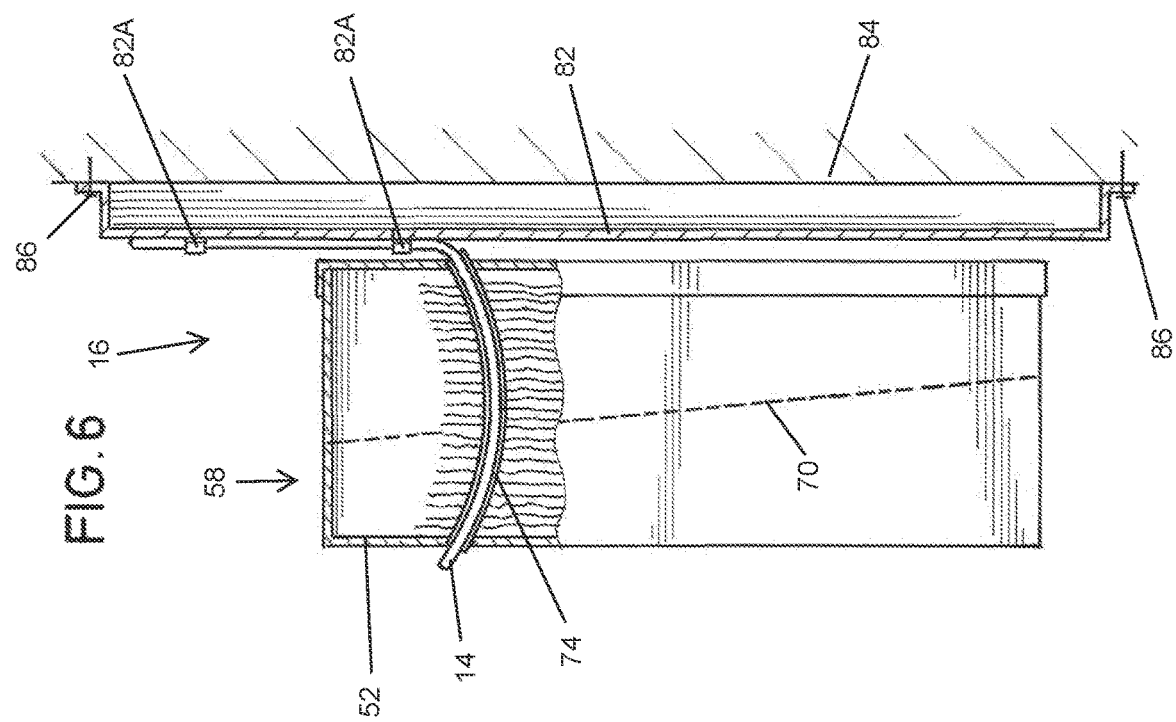

US 11,457,988 B1

GLOVE DISPENSING SYSTEM AND GLOVES FOR USE THEREIN

FIELD OF THE INVENTION

The present invention relates to systems for dispensing gloves, primarily disposable gloves, such as those used in healthcare facilities.

BACKGROUND OF THE INVENTION

The use of gloves of various types in health care facilities, e.g., hospitals, doctors' offices, rehabilitation facilities, etc., as well as facilities where food is handled and/or prepared, is ubiquitous. With particular respect to the use of gloves in health care facilities, the gloves generally come randomly distributed and oriented in a suitable box or dispenser, a portion of which can be torn away to provide an access window for a user to grab a glove. Because individual gloves must be pulled out of the box or dispenser, invariably a health care worker contacts the glove dispensing box with his or her bare hands, transferring any bacteria, viruses, or other pathogens that may have been on their hands. Subsequent users retrieving gloves from the glove dispenser likewise can pick up from and/or contaminate surfaces of the glove dispenser as well as the gloves in the dispenser with further pathogens. Further, putting the gloves on requires considerable two-hand manipulation.

SUMMARY OF THE INVENTION

In one aspect, the present invention relates to a glove dispensing system. In another aspect, the present invention relates to a glove dispensing system allowing a user to insert a hand into a glove with substantially no contact with the glove dispenser box.

In yet a further aspect, the present invention relates to a glove dispensing system which minimizes contamination by pathogens.

In still a further aspect, the present invention relates to a glove dispensing system which minimizes the degree of two-hand manipulation required for a user to insert a hand in a glove.

In an even further aspect, the present invention relates to a glove for use in a glove dispensing system.

These and further features and advantages of the present invention will become apparent from the following detailed description, wherein reference is made to the figures in the accompanying drawings.

BRIEF DESCRIPTION OF THE DRAWINGS

FIG. 3 is a perspective view of the container in one embodiment of the glove dispensing system of the present invention wherein the gloves are in a container.

FIG. 4 is a view taken along the lines 4-4 of FIG. 3.

FIG. 5 is a view taken along the lines 5-5 of FIG. 4.

FIG. 6 is a side, cross-sectional view of the container of FIG. 3 mounted on a wall.

FIG. 7 is a view similar to FIG. 6 wherein the lid of the container is removed.

DETAILED DESCRIPTION OF PREFERRED EMBODIMENTS

Figure 2:
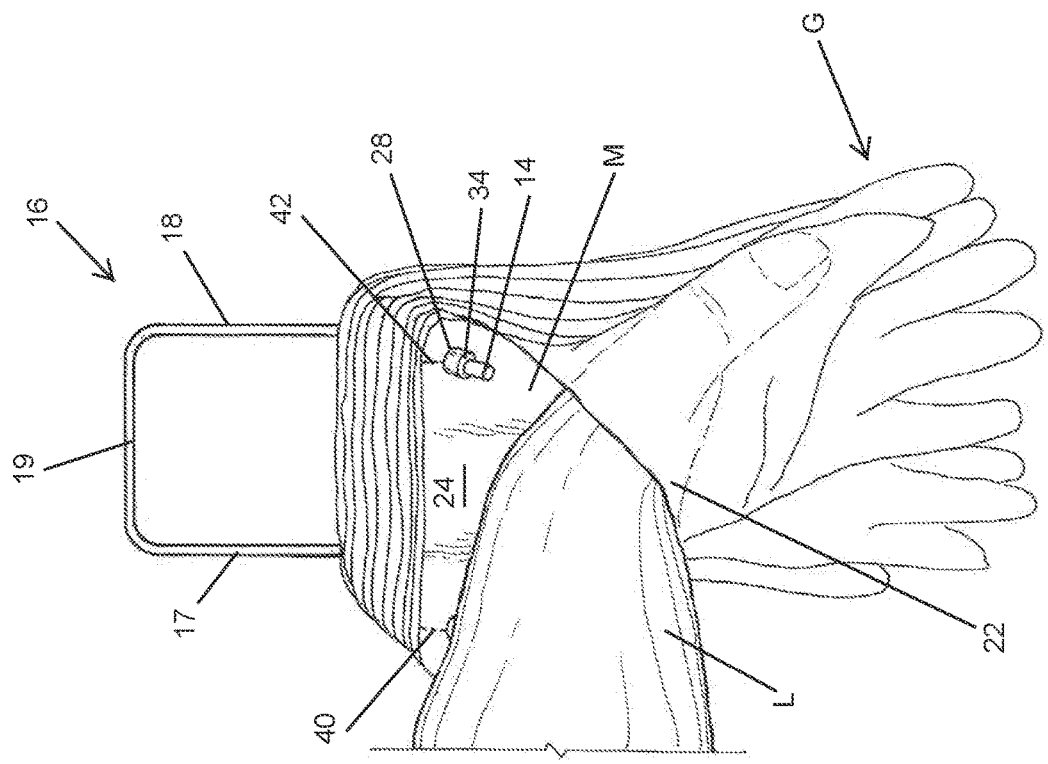
FIG. 2 is a view similar to FIG. 1 but showing a user inserting a hand into a glove.
Figure 1:
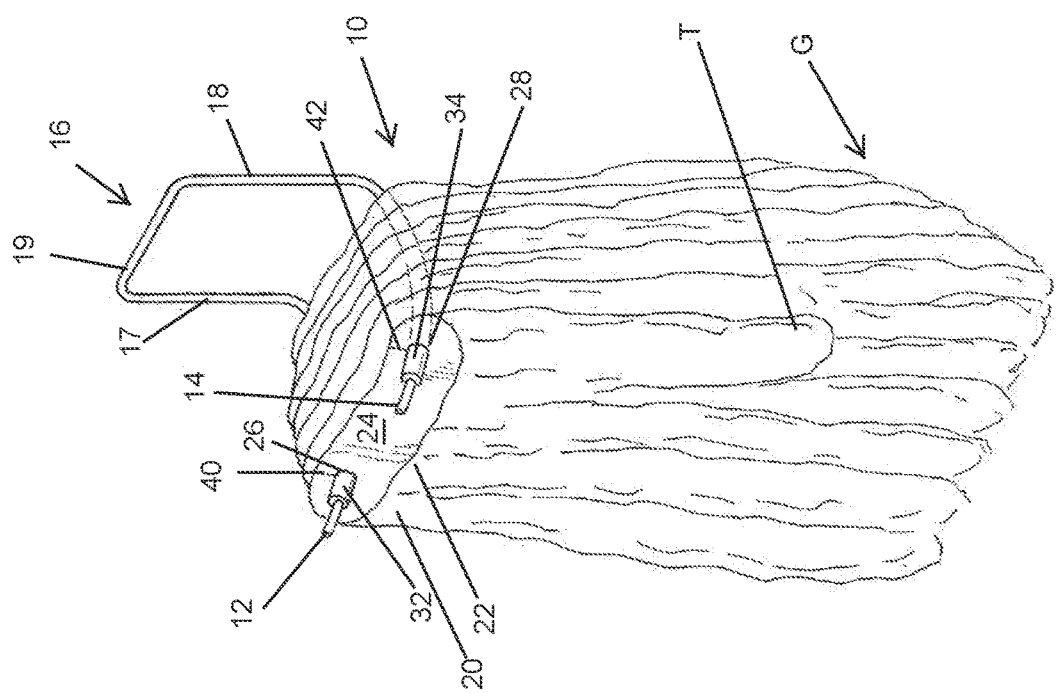
FIG. 1 is an isometric view of one embodiment of the glove dispensing system of the present invention.

Referring first to FIGS. 1 and 2 one embodiment, shown generally as 10, of the glove dispensing system of the present invention is depicted. The system 10 comprises a pair of laterally spaced tines or prongs 12 and 14, which as shown can be curved and which can be connected to a U-shaped frame shown generally as 16 having a first leg 17, a second leg 18, a cross-piece 19. As can be seen, tines 12 and 14 are connected to legs 17 and 18, respectively, of frame 16 and it will be appreciated that preferably, frame 16 together with tines 12 and 14 are formed as a monolithic piece. It will be understood that frame 16 can be attached to a surface, generally a vertical surface, that will allow tines 12 and 14 to project laterally outwardly. It is also to be understood that tines 12 and 14 can be individually connected to any surface which allows the tines 12 and 14 to project laterally outwardly.

Received on tines 12 and 14 are a plurality or cartridge of gloves G, gloves G comprising a glove body for receiving the palm of the hand and finger and thumb receiving formations as is well known to those skilled in the art. Gloves G also have a peripherally extending cuff 20 having a front wall 22 and a back wall 24, there being perforations, e.g., apertures or openings, 26 and 28 in back wall 24 which are laterally spaced, the spacing being substantially the same as the lateral spacing of the tines 12, 14. In the embodiment shown in FIGS. 1 and 2, the gloves G are generally disposed such that a left hand L (see FIG. 2) can be inserted into the glove G with minimal two-hand manipulation. As can be seen, particularly with reference to FIG. 2, the gloves G are hanging generally vertically downwardly from the tines 12 and 14. In this regard, the perforations 26 and 28 are in back wall 24 such that front wall 22 naturally tends to fall downwardly away from wall 24 providing a mouth M into which a hand, in this case the left hand L, can be slid.

It will also be recognized that if the position of the gloves G shown in FIG. 1 was reversed by 180°, the front wall 22 would become the back wall 22 and the perforations 26 and 28 would then be in back wall 22 (formerly front wall 22), the thumb portion T would then be positioned to the left with reference to FIG. 1, meaning that the right hand could be slipped into the mouth M formed between front and back walls in the same manner as shown with respect to the left hand L being shoved into glove G of FIG. 2. In this regard, and as well known to those skilled in the art, surgical gloves and other disposable gloves are generally ambidextrous so that any one glove can fit on either the left or the right hand. In this regard, it will be understood that terms such as "back wall", "front wall", "back side," "front side" is with reference to the orientation of the gloves when they are hanging on the tines ready for use by a user.

In the embodiments shown in FIGS. 1 and 2, it can be seen that the gloves G are carried on first and second tubular members 32 and 34, respectively. During the manufacturing and packaging process, the gloves G could be mounted on the tubular members 32 and 34 which can be flexible and allow a plurality or cartridge of gloves G to be provided. Since the tines 12 and 14 have a smaller outside diameter (OD) than the inside diameter (ID) of the tubes 32 and 34, respectively, the tubes easily slip over the tines to provide ready access to the gloves G. The use of tubes 32 and 34 is simply one way the gloves G can be supplied in "cartridges"

wherein a plurality of gloves can easily be mounted on the tines 12 and 14. It will be recognized that rather than use of the tubes 12 and 14, the individual gloves G can have reinforcing donuts in encircling relationship to the perforations 26 and 28. Regardless of how the gloves G are packaged into cartridges or groups, the gloves G will generally have tear lines or perforations such as indicated at 40 and 42, such that when a hand is inserted into one of the gloves G, and a downward force is exerted, the tear lines 40, 42 will allow the glove to be separated from the tines or other such carrier without the glove being irregularly ripped or frayed.

Referring now to FIGS. 3-5, there is shown an embodiment of the present invention wherein a plurality or cartridge of gloves G are disposed in a container or box which can be attached to spaced tines or in some other way well known to those skilled in the art to a surface which allows the gloves G carried by the container or box to hang generally vertically when in the use position. Referring then to FIG. 3, there is shown a container or box 50 having a first or front wall 52, a lid 54 providing a second or back wall 56, a top wall 58, a bottom wall 60, a first side wall 62, and a second side wall 64. Container 50 has a tear away section S delineated by a peripherally extending tear-line 70 which, as can be seen from FIGS. 3 and 4, is in both side walls and the top and bottom walls. Tear line 70 can be conveniently formed by a series of perforations well-known to those skilled in the art, whereby tear away section S including first or front wall 52 and second or back wall 56 is formed. As seen in FIG. 4, the ends of the tubes 72, 74 extending through second or back wall 56 can be fixed to an annular retainer 76 which prevents the tubes 72, 74 from being easily dislodged from the container 50. In this regard, the retainer 76 can be glued or otherwise affixed to back wall 56, albeit such is not necessary.

By comparing FIGS. 2 and 5, it can be seen that in the embodiment shown in FIG. 5, the gloves G have the same orientation and features as described above with respect to the embodiments of FIGS. 1 and 2. Thus, as particularly seen in FIG. 5, the cuff of the gloves G has a back wall 24 and a front wall 22, the front wall 22 naturally falling slightly outwardly away from back wall 24 to provide the mouth M through which a user's hand can be slipped into the body of the glove G.

Referring now to FIGS. 6 and 7, the container 50 containing the gloves G as described with reference to the embodiment of FIGS. 3-5 is shown mounted on the tines 12 and 14. As shown in FIGS. 6 and 7, and as depicted in FIGS. 1 and 2, the tines 12 and 14 are slightly curved, and tubes 72, 74 are flexible such that when the tubes are placed on the tines, the tubes conform to the curve of the tines. Also as seen in FIGS. 6 and 7, the tines 12 and 14 are part of frame 16 which can be secured by fasteners 82A to a mounting frame 82 which in turn can be secured to a vertical support such as wall 84 by fasteners 86, extending through flanges 82B of frame 82. It will be appreciated that frame 16 can be attached directly to wall 84 rather than mounting frame 82. It will also be appreciated that the tines 12 and 14 can be adapted such as to be directly attachable to wall 84 or other suitable support surface which allows the gloves G to hang generally vertically when positioned for use.

Figure 8:
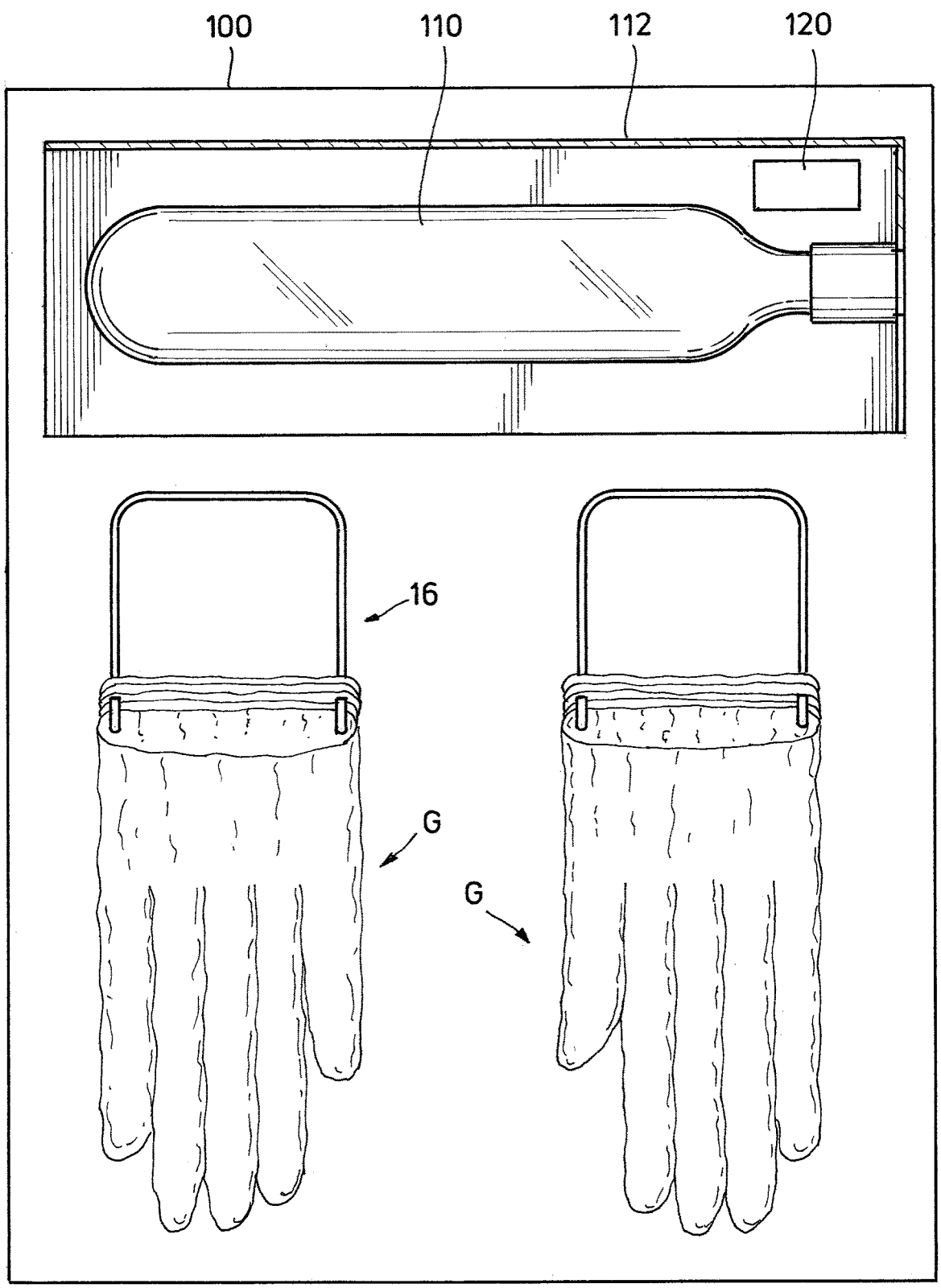
FIG. 8 is another embodiment of the present invention wherein a UV light is disposed above the gloves.

Turning to FIG. 8, there is shown another embodiment of the present invention. In the embodiment of FIG. 8, gloves G are mounted in a container 100 which is mountable to a wall or other surface similar to the embodiment shown in FIGS. 6 and 7. An ultraviolet (UV) light source 110 is mounted in container 100 above gloves G such that disinfecting wavelengths of UV light can shine on gloves G. UV light source 110 is positioned within a housing 112 which directs the UV light onto gloves G and also protects nearby persons from prolonged UV light exposure. UV light source 110 can be powered by batteries or have an electrical cord/plug (not shown). UV light source 110 can be activated/deactivated manually by an external switch or power button (not shown). In a preferred embodiment UV light 110 is automatically activated/deactivated by a motion sensor 120. Motion sensor 120 can be operably connected to a timer (not shown) to ensure UV light source 110 only remains on for a predetermined period of time. The system of the present invention can be programmed to activate UV light source 110 for a desired period of time upon triggering motion sensor 120. In this regard, a user would approach the glove dispenser and wave his/her hand over motion sensor 120. The motion activates the UV light for a desired number of seconds. This ensures that gloves G are thoroughly disinfected immediately before use. The system of the present invention may also use a combination of power switch and motion sensor. In such case, UV light source 110 remains on except when motion sensor 120 is triggered. This ensures the gloves G are disinfected by UV light, but prevents exposing the users to UV light when inserting their hands into gloves G. It will be well understood by those skilled in the art that the activation/deactivation of UV light source 110 can be programmed in many ways to meet the specific needs of the user. UV light source 110 can be of any type well known to those skilled in the art, including but not limited to mercury vapor bulbs or light emitting diodes (LEDs). UV light source 110 can emit UV-A, UV-B, or UV-C wavelengths. It will further be appreciated that the exact number and placement of UV light source 110 can vary as desired.

Although specific embodiments of the invention have been described herein in some detail, this has been done solely for the purposes of explaining the various aspects of the invention and is not intended to limit the scope of the invention as defined in the claims which follow. Those skilled in the art will understand that the embodiments shown and described are exemplary, and various other substitutions, alterations, and modifications, including but not limited to those design alternatives specifically discussed herein, may be made in the practice of the invention without departing from its scope.

What is claimed is:

1. A glove dispenser system comprising:
   first and second tines adapted to be attached to and project laterally outwardly from a support in laterally spaced relationship;
   a plurality of gloves, each of said gloves having a front side and a back side, each of said gloves further comprising a peripherally extending cuff having a front wall, a back wall, and an outer edge, there being a pair of first and second laterally spaced perforations in the back wall of said cuff, whereby said gloves hang generally vertically from said tines with said front wall facing outwardly from said support when said tines are attached to said support; and
   a frame having a U-shaped portion with spaced first and second legs, said first leg being connected to said first tine, said second leg being connected to said second tine, said U-shaped portion being adapted to be attached to said support.

2. The system of claim 1, wherein said first and second perforations comprise first and second holes, respectively.

3. The system of claim 1, wherein said plurality of gloves are removably mounted on first and second tubes extending through said first and second perforations, respectively.

4. The system of claim 3, wherein said first and second tubes are receivable on said first and second tines, respectively.

5. The system of claim 1, wherein there is a first tear line extending from said first perforation to said outer edge of said cuff, and a second tear line extending from said second perforation to said outer edge of said cuff.

6. The system of claim 5, wherein each of said first and second tear lines comprise a first and second series of perforations, respectively.

7. The system of claim 4, wherein said gloves mounted on said tubes are carried in a container, said container having a first wall and an opposed second wall, said tubes having first ends extending through said first wall and second ends extending through said second wall.

8. The system of claim 7, wherein said container has a tear away section.

9. The system of claim 8, wherein said container has a bottom wall and a top wall and said container has a peripherally extending tear line to produce said tear-away section of said container including said first wall.

10. The system of claim 7, wherein said container containing said gloves is received on said tines.

11. The system of claim 1, further comprising at least one UV light source positioned near said gloves and operable to shine disinfecting wavelengths of light on said gloves.

12. The system of claim 11, further comprising at least one motion sensor for activating and/or deactivating said at least one UV light source.

13. A glove for use in a glove dispensing system, comprising:
    a glove body, finger and thumb receiving projections, said glove body having a front side and a back side, and a peripherally extending cuff having a front wall, a back wall, and an outer edge, there being a pair of first and second laterally spaced perforations in the back wall of said cuff, wherein there is a first tear line extending from said first perforation to said outer edge of said cuff, and a second tear line extending from said second perforation to said outer edge of said cuff.

14. The system of claim 13, wherein said first and second perforations comprise first and second holes, respectively.

15. The system of claim 13, wherein each of said first and second tear lines comprise a first and second series of perforations, respectively.

16. A system for dispensing the glove of claim 13, comprising:
    first and second tines adapted to be attached to and project laterally outwardly from a support in laterally spaced relationship;
    at least one of said gloves whereby said at least one of said gloves hangs generally vertically from said tines with said front wall facing outwardly from said support when said tines are attached to said support.

17. The system of claim 16, further comprising at least one UV light source positioned near said gloves and operable to shine disinfecting wavelengths of light on said gloves.

18. A glove dispenser system comprising:
    first and second tines adapted to be attached to and project laterally outwardly from a support in laterally spaced relationship;
    a plurality of gloves, each of said gloves having a front side and a back side, each of said gloves further comprising a peripherally extending cuff having a front wall, a back wall, and an outer edge, there being a pair of first and second laterally spaced perforations in the back wall of said cuff, whereby said gloves hang generally vertically from said tines with said front wall facing outwardly from said support when said tines are attached to said support, wherein said plurality of gloves are removably mounted on first and second tubes extending through said first and second perforations, respectively, and wherein said first and second tubes are receivable on said first and second tines, respectively.

19. The system of claim 18, wherein said gloves mounted on said tubes are carried in a container, said container having a first wall and an opposed second wall, said tubes having first ends extending through said first wall and second ends extending through said second wall.

20. The system of claim 18, further comprising at least one UV light source positioned near said gloves and operable to shine disinfecting wavelengths of light on said gloves.

\* \* \* \* \*